(12) United States Patent
Jarvik

(10) Patent No.: US 6,227,820 B1
(45) Date of Patent: May 8, 2001

(54) AXIAL FORCE NULL POSITION MAGNETIC BEARING AND ROTARY BLOOD PUMPS WHICH USE THEM

(76) Inventor: Robert Jarvik, 333 W. 52nd St., New York, NY (US) 10019

(*) Notice: Subject to any disclaimer, the term of this patent is extended or adjusted under 35 U.S.C. 154(b) by 0 days.

(21) Appl. No.: 09/412,493

(22) Filed: Oct. 5, 1999

(51) Int. Cl.[7] ............................. F04B 17/00; F04B 35/04

(52) U.S. Cl. ................. 417/423.12; 417/356; 600/131

(58) Field of Search ..................... 417/423.3, 356, 417/423.12, 423.8; 600/16, 131

(56) References Cited

U.S. PATENT DOCUMENTS

| | | | |
|---|---|---|---|
| 5,507,629 | * | 4/1996 | Jarvik ............................. 417/423.3 |
| 5,707,218 | * | 1/1998 | Maher et al. ......................... 417/356 |
| 5,928,131 | * | 7/1999 | Prem ................................ 600/16 |
| 5,951,263 | * | 9/1999 | Taylor et al. ....................... 417/356 |
| 5,957,672 | * | 9/1999 | Aber ............................... 417/423.12 |
| 6,015,272 | * | 1/2000 | Antaki et al. ..................... 417/356 |
| 6,074,180 | * | 6/2000 | Khanwilkar et al. ............. 417/356 |
| 6,080,133 | * | 6/2000 | Wampler ........................... 600/131 |
| 6,093,001 | * | 7/2000 | Burgreen et al. ................ 417/423.8 |

* cited by examiner

Primary Examiner—Teresa Walberg
Assistant Examiner—Leonid Fastovsky

(57) ABSTRACT

A generally cylindrical rotor very closely confined between two rigid thrust bearing surfaces is radially suspended by an array of attracting or repelling magnets or by a combination of permanent magnets and ring shaped members composed of ferromagnetic material. The geometry permits very small spacing between magnetic components to achieve high radial stiffness. High magnetic axial forces exerted between the rotor and stationary component on one end of the rotor are counter-balanced by equal and opposite forces at the other end of the rotor. Precise positioning of the rotor in the location where the opposing axial magnetic forces counter-ballance each other yields a net magnetic axial force on the rotor of near zero, hence the reference to this as the null position. Wear resistant mechanical thrust bearings confine the rotor axially to maintain this position during rotatioin. Precisely balance the magnetic axial forces in the proper geometry with relation to the mechanical thrust bearings. Blood pumps utilizing this type of bearing are disclosed, including both axial flow pump and centrifugal flow pump configurations with high flow washing of the junction of the rotating and stationary parts to prevent thrombus accumulation.

15 Claims, 3 Drawing Sheets

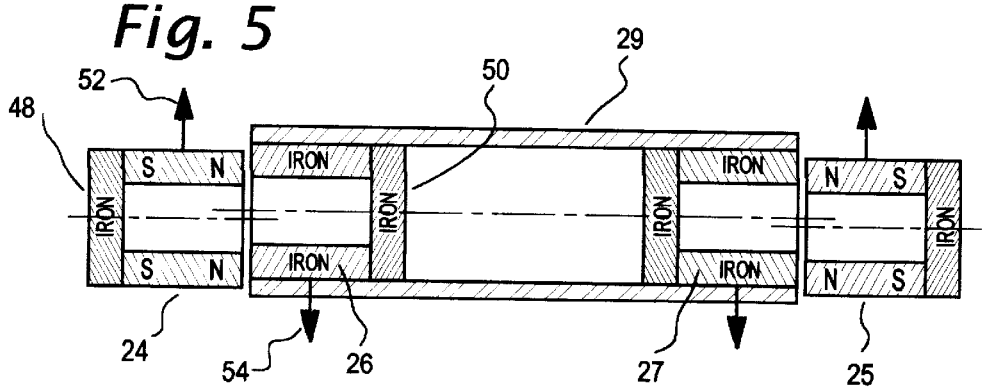
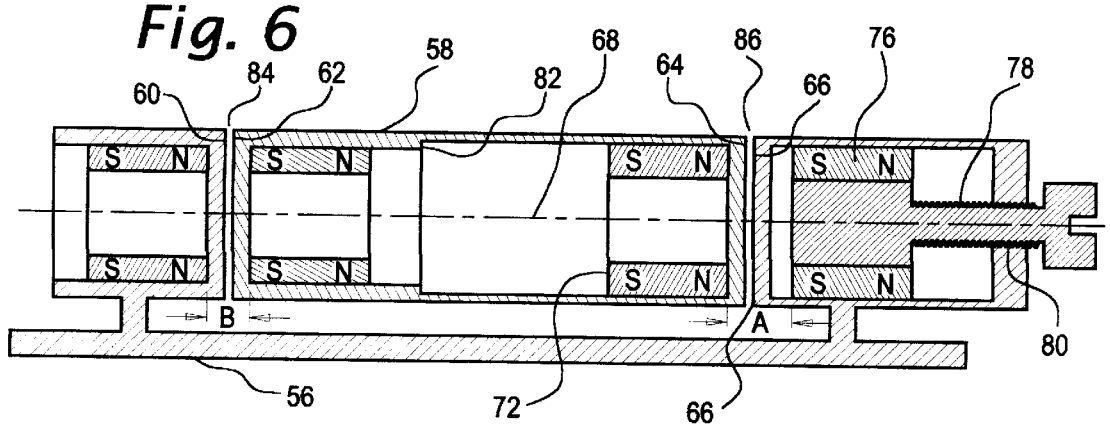
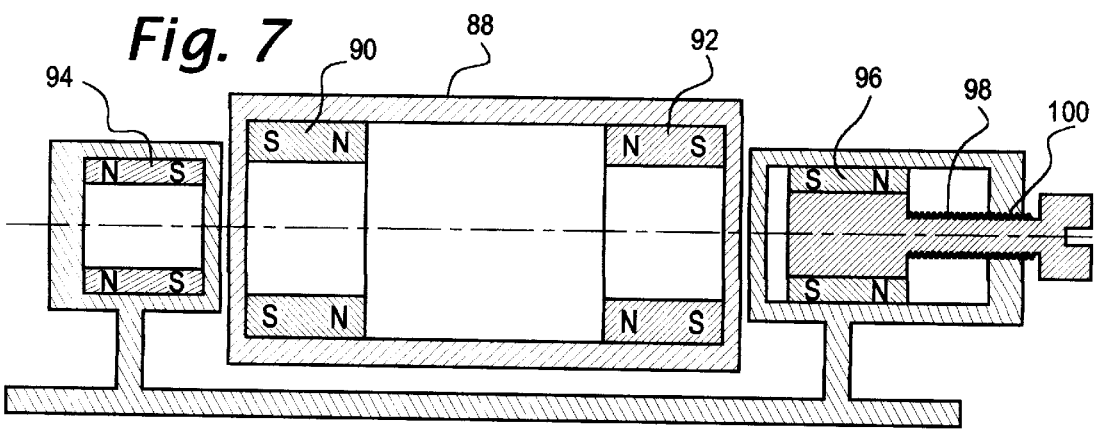

AXIAL FORCE NULL POSITION MAGNETIC BEARING AND ROTARY BLOOD PUMPS WHICH USE THEM

BACKGROUND OF THE INVENTION

Rotary blood pumps having magnetically supported or partially magnetically supported bearings have advantages including low wear, low thrombogenicity, and long durability. The inventors of prior art devices have generally sought to suspend a rotating impeller utilizing various types of sensors and feedback control methods similar to those used with general purpose magnetically suspended bearings. The objective of completely magnetically suspended blood pumps has been to provide wide clearance gaps between the rotating impeller and other parts of the device so that blood could flow through the gaps to avoid stagnation and clotting. Complete elimination of contact between rotating and stationary parts has the advantage of avoiding friction and heat generation which can damage blood. Olsen U.S. Pat. No. 4,688,998, and Moise U.S. Pat. No. 4,779,614 utilized sensors and servo-control systems of the general type described to obtain full magnetic suspension, however none of these or other fully magnetically suspended blood pumps has proved clinically successful due to their large size and complexity or to other unsolved problems.

Jarvik, U.S. Pat. No. 4,994,078, discloses blood pumps having blood immersed mechanical radial bearings and partial magnetic thrust bearings. High velocity washing of the junction of the rotating and stationary components of various embodiments of this invention has proven successful and several devices incorporating this principle have functioned successfully for many months in animals and one design has been successfully used in human patients. Jarvik U.S. Pat. No. 5,507,629, discloses blood pumps with radial magnetic bearing support and mechanical thrust bearing support, in which the mechanical bearing is also washed by high blood flow. Wampler, U.S. Pat. Nos. 5,840,070 and 5,695,471 disclose similar devices having partial magnetic bearing support together with mechanical thrust bearings. Like Jarvik, U.S. Pat. No. 5,507,629 the magnetic forces which support the rotor radially are exerted across relatively wide channels through which blood flows. The magnitude of the magnetic forces and size of the gaps across which they are exerted limits the stiffness of the radial bearing and the rotors of these devices are subject to either radial or axial displacement due to blood flow and pressure forces as well as shock, vibration and other inertial forces.

The present invention improves upon previous partially magnetically suspended blood pumps by minimizing the size of the magnetic components needed to achieve adequate radial stiffness. This permits miniaturization in the size of the overall pump which has important advantages, particularly when intraventricular placement is utilized (Jarvik, U.S. Pat. No. 5,092,879). Radial magnetic support is achieved by utilizing small very closely adjacent permanent magnets or a combination of permanent magnets and other non-magnetized ferromagnetic components. By this functional structure, the present invention permits stiffer radial bearings which has several important advantages regarding pump design and efficiency. The invention is distinguished from all prior magnetically suspended blood pumps because only a slight surface film of blood occupies the gap across which the suspending magnetic forces are exerted, and there is essentially no blood flow through this gap.

With "null position" magnetic bearings of the present invention the rotor is axially confined at each of its two ends by mechanical thrust bearings and is positioned extremely close to an axial position where there is no net magnetic axial force upon it in either direction. One embodiment of the invention includes means to precisely adjust the axial forces produced by the permanent magnets to locate the null position within a very tiny range of axial motion permitted by mechanical thrust bearings. The thrust bearings also stablize the rotor by preventing tilt with regard to the axis of rotation.

OBJECTS OF THE INVENTION

It is an object of the present invention to provide a passive permanent magnet bearing system to support radial loads together with a mechanical thrust bearing device designed to experience virtually zero thrust load as a result of magnetic forces.

It is a further object of the invention to provide a passive magnetic radial bearing which utilizes magnetic components placed in close proximity to each other to achieve high radial stiffness.

Another object of the invention is to provide a very small diameter passive radial magnetic bearing system suitable for use in rotary blood pumps.

A still further object of the present invention is to provide hydrodynamic rotary blood pumps utilizing "null position" passive radial magnetic bearings with axial thrust bearing confinement in configurations suitable for intraventricular implantation.

Another object of the invention is to provide passive radial magnetic bearings small enough and stiff enough to support the rotor of a miniature axial flow blood pump at both ends of the hub of the impeller.

A further object of the invention is to provide a bearing system for rotary blood pumps which is entirely stable and permits the pump rotor to remain in its usual functional position when shut off without risk of damage during shutdown and without the need for rotor displacement limiting devices.

A still further object of the invention is to improve the design of partially magnetically suspended rotary blood pumps and make them fully practical for widespread human application to support heart function for longer than a decade.

THE FIGURES

FIG. 5 is a longitudinal section of the ferromagnetic components mounted within a tube which can function as the rotor of a bearing system according to the present invention, and also showing in longitudinal section a ring magnet with a disc of back iron at each end of the rotor.

FIG. 6 is a longitudinal section of a complete bearing system according to one embodiment of the invention in which the rotor is supported radially by attracting magnetic forces.

FIG. 7 is a longitudinal section of another embodiment of the invention in which the rotor is supported radially by repelling magnetic forces.

SPECIFIC DESCRIPTION OF THE INVENTION

Figure 1A:
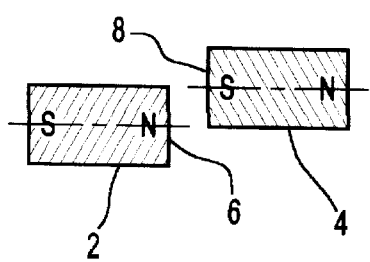
FIG. 1A is a longitudinal sectional drawing of two bar cylindrical magnets with the axis of each displaced laterally from the axis of the other.
Figure 1B:
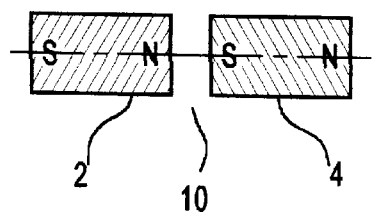
FIG. 1B is a longitudinal section of the same magnets attracted together with their axes aligned.
Figure 1C:
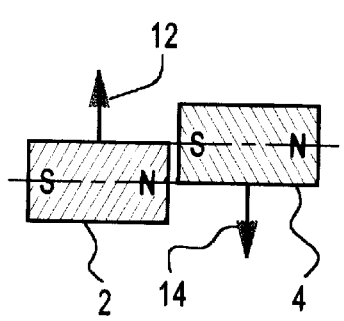
FIG. 1C illustrates the same two magnets touching on their ends and illustrating by vectors the net forces tending to bring them into alignment as shown in FIG. 1B.

FIG. 1 illustrates the functional principle of axial alignment utilized in the present invention. Two cylindrical bar magnets are shown in FIG. 1A positioned near one another with their opposite poles attracting one another. If the end surfaces, 6,8, are highly polished and lubricated, when the two magnets make contact they will take the position shown in FIG. 1B where the axes of each cylinder are aligned and the two faces meet at plane 10. If the two magnets are displaced laterally from one another, as shown in FIG. 1C, so that their faces contact but their axes are out of alignment, forces illustrated by the force vectors 12, 14 will be generated by their magnetic fields in a direction to restore axial alignment.

Figure 2:
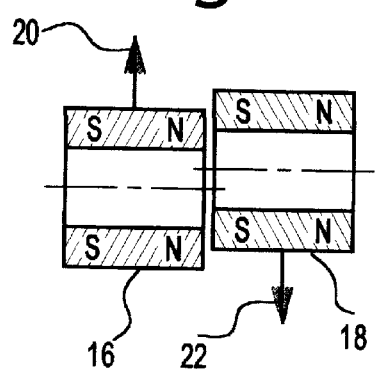
FIG. 2 is a longitudinal section of two ring magnets axially offset.

FIG. 2 illustrates similar magnetic forces upon two ring magnets which are also generally cylindrical in shape and have flat faces at right angles to the axis of the cylinder. Magnets 16 and 20 in the position shown experience force vectors 20 and 22 tending to align their cylindrical axes.

Figure 3:
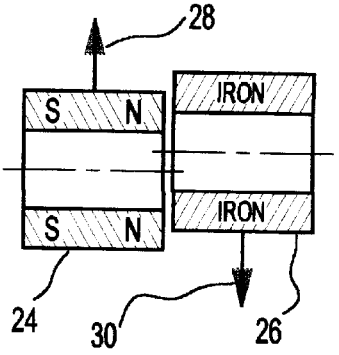
FIG. 3 is a longitudinal section of one ring magnet and a ring of iron of similar geometry, illustrating the magnetic forces tending to align their axes.

FIG. 3 shows similar force vectors 26, 28 acting to align a ring magnet 24 and a cylindrical ring of iron, 26.

Figure 4:
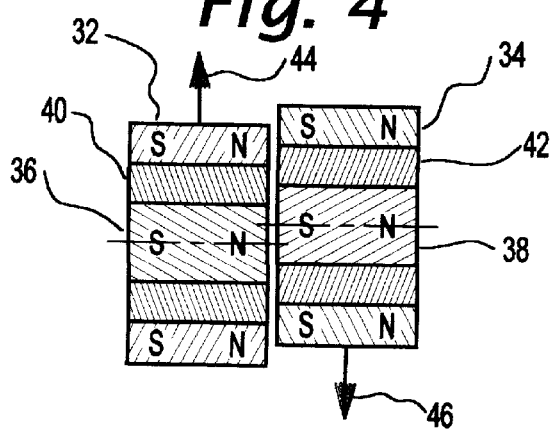
FIG. 4 is a longitudinal section of two ring magnets each having a bar magnet held centered within its bore by a ring shaped spacer.

FIG. 4 shows two arrays each comprising a ring magnet 32,34, a bar magnet, 36, 38, and a ring spacer of non-magnetic material such as polymer or ceramic, 40,42. Net force vectors 44, 46, tend to align the arrays with more force than there would be if the bar magnets 36, 38 were not present. Other concentric arrays having additional thinner ring magnets could be designed to create an even stronger force vector tending to axially align them.

FIG. 5 shows the use of ferromagnetic end pieces to concentrate the magnetic flux and increase the forces tending to axially align the magnets. End pieces 48, 50 are discs of ferromagnetic material such as iron. When used in the position shown they increase the force vector tending to axially align the two hollow cylinders, 24,26. This is indicated by the use of longer force vector arrows 52,54 compared to the those shown in FIG. 3 (28,30) for the same parts 24,26 without the ferromagnetic flux return path. In FIG. 5, two sets of ring magnets 24, 25 are shown with two iron rings 26,27 mounted within a sleeve 29. The structure comprised of the sleeve and iron rings is adapted to serve as a rotor radially supported for rotation about its axis by the magnets 24,25. This may be accomplished using means such as a frame like the one shown in FIG. 6. This arrangement of permanent magnets and non-magnetized ferromagnetic material demonstrates one embodiment of the present invention in which the rotor has neither permanent magnets nor electromagnets mounted thereupon.

FIG. 6 illustrates the principle of the bearing of the present invention and the achievement of the magnetic axial counter-balanced null position to minimize the magnetic forces on the mechanical axial thrust bearings by use of an adjustment screw. The bearing system includes a rigid stationary frame 56 having a generally cylindrical rotor 58 mounted in a position which is axially confined by thrust bearing surfaces 60,62 and 64,66. These surfaces are precisely perpendicular to the axis of rotation of the rotor 68, and fabricated of highly polished wear resistant material such as diamond coated titanium. Permanent ring magnets 70,72 magnetized with the polarity shown, are bonded into the rotor precisely concentric to its axis of rotation. Two additional ring magnets 74,76 are mounted to the frame in concentric alignment to the axis of rotation of the rotor. Magnet 74 is pre-bonded in a fixed position as shown, but magnet 76 is mounted on an adjustment screw 78 which is engaged in threads 80 cut in the frame 56. By turning the screw the axial position of magnet 76 may be adjusted. For purposes of illustration, magnets 70 and 74 are shown as smaller in diameter then magnets 72 and 76. This is seen by noting the step in the rotor Inside diameter at 82. Assuming that all the magnets are fabricated of the same material (such as Neodymium iron boron) and are magnetized to the same energy product, the axial attractive force between magnets 72,76 will be greater at an equivalent distance of separation than the attractive force between the other pair of magnets 70,74. By means of the adjustment screw 78 the distance of separation between magnets 72 and 76 indicated at "A" can be adjusted so that the axial force between magnets 72 and 76 exactly equals the force between magnets 70 and 74 which are closer together as illustrated by the distance labeled "B" since distance "A">distance "B". In real embodiments of the invention, with exact measurements of the strength of the magnetic pairs and selection of perfectly matched sets of magnets, adjustment during assembly might not be necessary.

At the two thrust bearing ends of the rotor, gaps 84 and 86 exist between the rotor and the stationary parts of the device. The rotor will move to one direction and make contact so as to eliminate the gap on whichever side of the rotor experiences higher axial magnetic forces. Because it is axially unstable except as mechanically confined. If all the parts are fabricated with great precision, and the mating surfaces are all precisely perpendicular to the axis of rotation of the rotor, then it is possible to reduce both gaps to virtually zero distance. In this theoretical case if the spacing and force of the magnets is adjusted so that zero axial force is exerted in either axial direction by the rotor against the stationary parts of the device, this defines the magnetic axial force null position. For a device operating at close to constant temperature, such as a blood pump implanted within the body, dimensional changes due to thermal expansion and contraction are minimal and probably require no special design for compensation. In other devices, rotating and stationary parts fabricated of materials having different coefficients of expansion may be combined to give virtually no change in the gap dimensions over a range of operating temperatures.

In practical reality the parts cannot be made with gaps 84 and 86 equal to zero. A slight gap such as 50 millionths of an inch (0.000050") on each side of the rotor would allow the rotor to move into contact with one side. Then one gap would be zero, and the other gap would be one ten-thousandth of an inch (0.0001"). With the axis of the rotor horizontal, by changing the spacing of magnets 72 and 76 by means of the adjustment screw 78, a position very close to the null position can easily be found if either gap 84 of 86 is observed under magnification. The gap viewed is seen to change from either near zero (closed) to about 0.0001" (open), or vice versa, as the adjustment causes the net magnetic axial force on the rotor to displace it. A delicate position of adjustment will be found where slight additional turns of the adjustment screw first in one direction and then in the other will cause the rotor to move back and forth between two axial positions, alternately opening and closing the observed gap. If an anti-backlash screw is used and the rotational position of the screw is measured at the two screw positions where the rotor moves axially, a midway setting for the screw position may be selected and the screw then locked in that position. This is very close to the magnetic null axial force position which would exist if the rotor were fixed with an equal gap of 0.000050" on each side. In some embodiments of the invention, adjustment of the position of the magnets on each end of the device (with the rotor between them) may be provided, such as by using two adjustment screws.

If axial forces applied to the rotor during operation (such as fluid pressure forces if the rotor is part of a pump) are ignored for the sake of this discussion of the forces related to magnetic bearing, it is apparent that the rotor will contact the mechanical thrust bearing surface on one end due to a slight net magnetic axial force in one direction. The magnitude of that force will depend on the strength of the axial magnetic forces acting on each end of the rotor, and the relationship of the change in force as a function of displacement. If high strength magnets are used, or the magnet's mass is relatively large, the radial stiffness of the bearing will be more than with weaker magnets or magnets of less mass. In general, the magnetic forces required to achieve a stiffer radial bearing of a given size will require a smaller gap for a given magnetic load against the thrust surfaces. With small magnetic bearing magnets less than 0.5" diameter suitable for rotary blood pumps and with precise axial force balancing, the net axial force measured as a function of axial displacement from the null position may be as high as 1000 lbs/inch without excessive force on the thrust bearing surfaces. With 1000 lbs/inch force and proper adjustment of the magnets to achieve the null position as discussed above, the axial force resulting from a displacement of only 0.000050" from the null position would only be 0.05 pounds. With an radial stiffness of only 500 lbs/inch the bearing system supports a rotor weighing 0.1 lb (typical for a miniature axial flow pump rotor) with an off axis radial displacement of only 0.0002". The radial bearing supports 1 lb with a radial displacement of only 0.002" and supports even higher radial loads at a greater off axis displacement. With magnets and spacing chosen to give forces similar to these we see that an embodiment of the present invention would exert an axial force on its thrust bearings of less than 5% of the radial load bearing capacity.

In the bearing system shown in FIG. 6 the thrust bearing surfaces also carry tilting loads which are applied to the rotor. In this layout, which uses attracting pairs of magnets at each end of the rotor, the polarity need not be north/south exactly as shown, so long as the two pairs attract. Other arrangements of magnets such as the one shown in FIG. 7 may be used, where repulsion rather than attraction occurs between the magnetic components at either end of the rotor. In FIG. 7, the rotor carries two axially magnetized ring magnets 90,92. The stationary frame of the device carries two other ring magnets 94,96 which are smaller such their outside diameter is approximately equal to the inside diameter of rotor magnets 90, 92. An adjustment screw 98 attached to magnet 96 and threaded through a hole in the frame at 100 permits the magnetic axial forces on the rotor to be balanced.

PREFERRED EMBODIMENTS OF THE INVENTION

Figure 8:
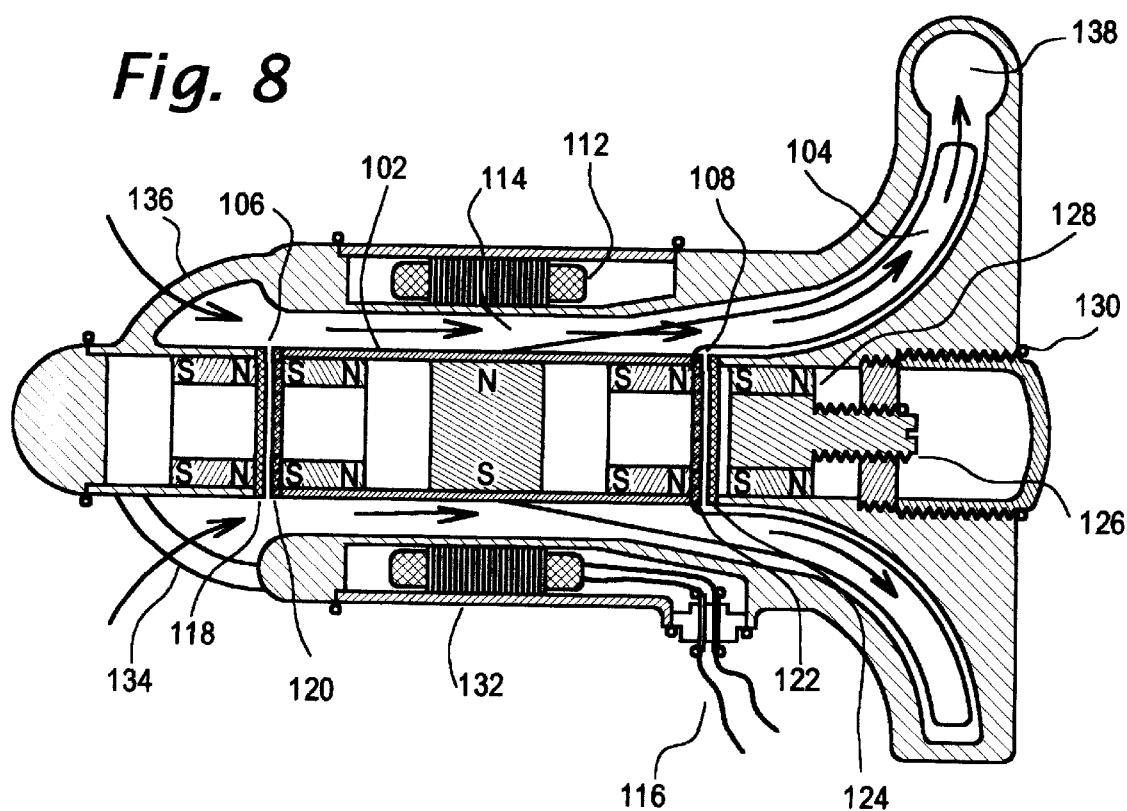
FIG. 8 is a longitudinal section of the preferred embodiment of a centrifugal blood pump utilizing the bearing system of the present invention.
Figure 9:
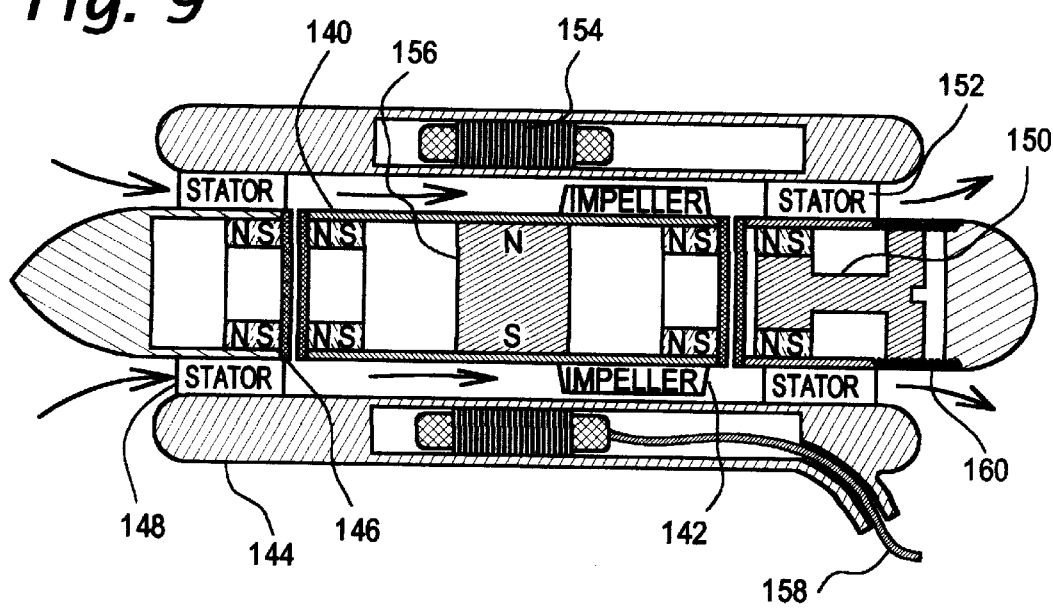
FIG. 9 is a longitudinal section of an axial flow pump utilizing the bearing system of the present invention.

FIGS. 8 & 9 illustrate the preferred embodiments of the invention in which axial force null position magnetic bearings are used to radially suspend the rotors of centrifugal and axial flow blood pumps. Referring to FIG. 8, a magnetic bearing arrangement similar to that shown in FIG. 6 supports a rotor 102, with a centrifugal pump impeller 104, by two pairs of ring magnets at each end of said rotor generally indicated at 106 and 108. A permanent magnet 110 utilized as part of a two pole electric motor which drives the impeller is magnetized side to side as illustrated. It is located midway on the impeller to maximize its separation from the magnetic bearing components at each end so that the magnetic forces of interaction between the motor magnet and bearing magnets will be low. A motor armature 112, having laminations and coils is disposed around the rotor and a annular channel 114 through which blood flows occupies the space between the said armature and the rotor. An electric cable 116 provides power to the motor windings. The housing and blood contacting components of the pump are preferentially fabricated of titanium with the exception of four ceramic thrust bearing discs 118, 120,122, 124, which are precision lapped and highly polished. The structure of the device is designed to permit welding and hermetic sealing of all spaces containing motor components and bearing magnets. A pacemaker type hermetic feedthrough 117 is provided for the wires. An adjustment screw 126 is used to adjust the precise axial position of magnet 128, and after this is completed the screw is welded in place at position 130. The pump housing 132 includes an inflow cage 134 which holds a hub 136 supporting the stationary inflow bearing components. The bearing gap between discs 118 and 120 can be viewed using a borescope inserted through the cage to permit excellent visualization during magnet position adjustment with screw 126. In FIG. 8 the arrows indicate the direction of blood flow into the pump, across the inflow bearing gap at 106, through the motor air gap 114 and then across the impeller 104 across the outflow bearing gap at 108, and out through the volute 138.

FIG. 9 illustrates another preferred embodiment where the bearing design is also similar to that shown in FIG. 6 and the rotor 140 carries the impeller of an axial flow pump 142. The housing 144, supports a stationary inflow hub 146 by support blades 148, and on the outflow side the housing supports an outflow hub 150 by outflow stator blades 152. In a fashion similar to that described for the centrifugal pump of FIG. 8, the blood flows through an annular channel between the rotor 140 and the motor armature 154. The rotor carries the motor magnet 156 which is also spaced approximately midway between the two sets of bearing magnets at either end of the rotor. An adjustment screw 160 is provided to permit positioning of the magnets properly.

In both blood pump designs illustrated the gap at the junction of the rotating and stationary components of the pump is very small and contains blood. The flow path of the pumps provides a high velocity stream of blood across these junctions to prevent all but a minimal amount of thrombus formation.

Referring to both FIGS. 8 and 9 one sees that the rotors of these pumps and their bearing systems are designed to locate the motor magnets radially centered within the motor bore. In the perfectly centered position, the lateral magnetic forces from each pole of the motor magnet pulling it to the side of the motor bore are counterbalanced. As the motor magnet is displaced away from the centerline of the motor bore the magnetic force pulling the rotor to one side increases and becomes very high if the rotor is allowed to move too far off center. Thus in the design of any radially suspended pump of this general layout it must be assured that the radial magnetic bearings are stiff enough to restore the motor magnet to its centered position if it becomes temporarily dislocated due to shock forces. If the radial magnetic bearings are not very stiff, radial limiting means may be required to prevent the motor magnet from becoming locked against the side of the motor bore. In the present invention, a major advantage of the bearing arrangements provided is that the radial stiffness of the magnetic bearings can be much higher than the stiffness of other permanent magnet bearing systems where blood flows through a gap across which radial magnetic bearing support force is exerted. This makes it possible to design the system so that no radial rotor position limiting means are required.

The information disclosed in the description of the present invention is intended to be representative of the principles I have described. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

I claim:

1. A passive radial magnetic bearing system adapted to support a rotor for rotation about an axis while it is axially confined by mechanical means, comprising,
    a. Rotor means mechanically free to rotate about an axis,
    b. Axial motion limiting means to permit said rotor means to rotate while closely confining it axially,
    c. Mechanical thrust bearing means affixed to said rotor means and to said limiting means,
    d. A first axially magnetized generally cylindrical permanent magnet mounted to said limiting means in alignment with the axis of rotation of said rotor means, adjacent to one end of said rotor means,
    e. A second axially magnetized generally cylindrical permanent magnet mounted to said limiting means in alignment with the axis of rotation of said rotor means, adjacent to the other end of said rotor means,
    f. Force transferring means, comprising a pair of generally cylindrical ferromagnetic structures mounted adjacent to each end of said rotor in axial alignment with the axis of rotation of said rotor which are subject to magnetic forces originating from said first and second permanent magnets to both support said rotor for radial rotation and force it against said thrust bearing means,
    g. Axial force balancing means comprising means to mount said magnets to said limiting means in position such that the net axial forces exerted on one end of said rotor by said first magnet are almost exactly counter-balanced by the axial forces exerted on the other end of said rotor by said second magnet.

2. The passive radial magnetic bearing system of claim 1 in which said rotor is so closely confined axially and said axial magnetic forces are so closely balanced that the net magnetic axial force exerted against said thrust bearing means is less than 5% of the radial load bearing capacity of the bearing.

3. The passive radial magnetic bearing system of claim 1 in which said first and second permanent magnets are mounted on the two ends of said rotor, and said force transferring means are mounted on said limiting means.

4. The passive radial magnetic bearing system of claim 1 in which one or both of said magnets may be moved along its axis to adjust the magnetic forces on the rotor by means of an adjustment screw, and after adjustment may be fixed in place.

5. The passive radial magnetic bearing system of claim 1 in which said first and second generally cylindrical magnets are bar magnets.

6. The passive radial magnetic bearing system of claim 1 in which said first and second generally cylindrical magnets are ring magnets.

7. The passive radial magnetic bearing system of claim 1 in which ferromagnetic pole pieces are used together with said permanent magnets to concentrate the magnetic flux and improve performance of the bearing system.

8. The passive radial magnetic bearing system of claim 1 in which said force transferring means constitutes a pair of magnets with one located at each end of said rotor.

9. The passive radial magnetic bearing system of claim 8 in which the polarity of said magnets is arranged such that magnetic axial forces of repulsion are exerted upon said rotor.

10. The passive radial magnetic bearing system of claim 1 in which one or more of said generally cylindrical permanent magnets is comprised of an array of two or more concentric ring magnets or a combination of ring magnets and bar magnets.

11. An hydrodynamic blood pump including,
    a. rotor means supported by passive magnetic radial bearing system means which exert opposing axial forces on the ends thereof,
    b. Mechanical confinement means closely axially confining said rotor between blood immersed mechanical thrust bearing means located at both ends, and,
    c. Means to adjust components of said passive magnetic bearing system to counter-balance said opposing axial magnetic forces such that when the net axial magnetic force on the rotor is zero, the rotor is within the range of axial positions to which it is confined by the mechanical thrust bearings.

12. The blood pump of claim 11 in which said confinement means prevent said rotor from moving an axial distance greater than 0.001".

13. The blood pump of claim 11 in which rotating permanent magnet means mounted within said rotor means impart torque to said rotor from electromagnetic fields produced by the armature of an electric motor.

14. An axial flow or centrifugal flow blood pump having impeller means supported by passive radial magnetic bearing means which utilize only stationary permanent magnets and require no rotating permanent magnets to achieve magnetic radial support.

15. The blood pump of claim 14 in which rotating permanent magnet means impart torque to said impeller from electromagnetic fields produced by the armature of an electric motor.

* * * * *